US007744910B2

(12) United States Patent
Gschneidner et al.

(10) Patent No.: US 7,744,910 B2
(45) Date of Patent: Jun. 29, 2010

(54) COMPOUNDS AND COMPOSITIONS FOR DELIVERING ACTIVE AGENTS

(75) Inventors: David Gschneidner, Thornwood, NY (US); Andrea Leone-Bay, Ridgefield, CT (US); Eric Wang, Ellicott City, MD (US); Lynn Errigo, Port Chester, NY (US); Koc-Kan Ho, Mount Kisco, NY (US); Jeffrey Bruce Press, Brewster, NY (US); Nai Fang Wang, Long Island City, NY (US); Pingwah Tang, Elmsford, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 793 days.

(21) Appl. No.: 11/531,602

(22) Filed: Sep. 13, 2006

(65) Prior Publication Data

US 2007/0010422 A1    Jan. 11, 2007

Related U.S. Application Data

(60) Continuation of application No. 11/173,075, filed on Jun. 30, 2005, now Pat. No. 7,186,414, which is a division of application No. 09/762,067, filed on Aug. 3, 2001, now Pat. No. 6,991,798, which is a continuation of application No. PCT/US99/17974, filed on Aug. 6, 1999.

(60) Provisional application No. 60/095,778, filed on Aug. 7, 1998, provisional application No. 60/098,500, filed on Aug. 31, 1998, provisional application No. 60/108,366, filed on Nov. 13, 1998, provisional application No. 60/119,207, filed on Feb. 5, 1999.

(51) Int. Cl.
| | |
|---|---|
| *A61K 9/00* | (2006.01) |
| *A61K 38/00* | (2006.01) |
| *A61K 51/00* | (2006.01) |
| *A61F 13/00* | (2006.01) |
| *A01N 37/18* | (2006.01) |
| *A61M 36/14* | (2006.01) |

(52) U.S. Cl. .................... 424/400; 424/1.69; 424/422; 514/2

(58) Field of Classification Search .................. None
See application file for complete search history.

(56) References Cited

U.S. PATENT DOCUMENTS

| | | |
|---|---|---|
| 3,489,793 A | 1/1970 | Bertelli |
| 4,061,466 A | 12/1977 | Sjoholm et al. |
| 4,147,767 A | 4/1979 | Yapel |
| 4,238,506 A | 12/1980 | Stach et al. |
| 4,442,090 A | 4/1984 | Kakeya et al. |
| 4,462,991 A | 7/1984 | Higuchi et al. |
| 4,757,066 A | 7/1988 | Shiokari et al. |
| 4,835,312 A | 5/1989 | Itoh et al. |
| 4,873,087 A | 10/1989 | Morishita et al. |
| 4,895,725 A | 1/1990 | Kantor et al. |
| 4,900,730 A | 2/1990 | Miyauchi |
| 4,925,673 A | 5/1990 | Steiner |
| 4,927,928 A | 5/1990 | Shroot et al. |
| 4,976,968 A | 12/1990 | Steiner |
| 4,983,402 A | 1/1991 | Steiner |
| 5,066,487 A | 11/1991 | Morelle et al. |
| 5,352,461 A | 10/1994 | Feldstein et al. |
| 5,401,516 A | 3/1995 | Milstein et al. |
| 5,443,841 A | 8/1995 | Milstein et al. |
| 5,447,728 A | 9/1995 | Milstein et al. |
| 5,451,410 A | 9/1995 | Milstein et al. |
| 5,455,335 A | 10/1995 | Kahane et al. |
| 5,540,939 A | 7/1996 | Milstein et al. |
| 5,541,155 A | 7/1996 | Leone-Bay et al. |
| 5,578,323 A | 11/1996 | Milstein et al. |
| 5,583,020 A | 12/1996 | Sullivan |
| 5,601,846 A | 2/1997 | Milstein et al. |
| 5,629,020 A | 5/1997 | Leone-Bay et al. |
| 5,643,957 A | 7/1997 | Leone-Bay et al. |
| 5,650,386 A | 7/1997 | Leone-Bay et al. |
| 5,667,806 A | 9/1997 | Kantor et al. |
| 5,693,338 A | 12/1997 | Milstein et al. |
| 5,705,529 A | 1/1998 | Matyus et al. |
| 5,709,861 A | 1/1998 | Santiago et al. |
| 5,714,167 A | 2/1998 | Milstein et al. |
| 5,750,147 A | 5/1998 | Kantor et al. |
| 5,766,633 A | 6/1998 | Milstein et al. |
| 5,773,647 A | 6/1998 | Leone-Bay et al. |
| RE35,862 E | 7/1998 | Steiner et al. |
| 5,776,888 A | 7/1998 | Leone-Bay et al. |
| 5,792,451 A | 8/1998 | Sarubbi et al. |
| 5,804,688 A | 9/1998 | Leone-Bay et al. |
| 5,811,127 A | 9/1998 | Milstein et al. |
| 5,820,881 A | 10/1998 | Milstein et al. |
| 5,824,345 A | 10/1998 | Milstein et al. |
| 5,840,340 A | 11/1998 | Milstein et al. |
| 5,863,944 A | 1/1999 | Leone-Bay et al. |
| 5,866,536 A | 2/1999 | Leone-Bay et al. |
| 5,876,710 A | 3/1999 | Leone-Bay et al. |
| 5,879,681 A | 3/1999 | Leone-Bay et al. |

FOREIGN PATENT DOCUMENTS

DE        25 22 474 A1    12/1975

(Continued)

OTHER PUBLICATIONS

Leone-Bay, A., "4-(4-Salicyloylaminophenyi)butyric Acid as a Novel Oral Delivery Agent for Recombinant Human Growth Hormone" Medi 006, Presented at the American Chemical Society, (Mar. 1996) New Orleans, LA.

(Continued)

*Primary Examiner*—Maury Audet
(74) *Attorney, Agent, or Firm*—Blank Rome LLP

(57) ABSTRACT

Compounds and compositions for the delivery of active agents are provided. Methods of administration and preparation are provided as well.

81 Claims, No Drawings

U.S. PATENT DOCUMENTS

| | | | |
|---|---|---|---|
| 5,935,601 A | 8/1999 | Leone-Bay et al. |
| 5,939,381 A | 8/1999 | Leone-Bay et al. |
| 5,955,503 A | 9/1999 | Leone-Bay et al. |
| 5,958,457 A | 9/1999 | Santiago et al. |
| 5,962,710 A | 10/1999 | Gschneidner et al. |
| 5,965,121 A | 10/1999 | Leone-Bay et al. |
| 5,972,387 A | 10/1999 | Milstein et al. |
| 5,976,569 A | 11/1999 | Milstein et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,051,258 A | 4/2000 | Kantor |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,071,538 A | 6/2000 | Milstein et al. |
| 6,084,112 A | 7/2000 | Ho et al. |
| 6,099,856 A | 8/2000 | Milstein et al. |
| 6,100,285 A | 8/2000 | Kantor |
| 6,100,298 A | 8/2000 | Leone-Bay et al. |
| 6,180,140 B1 | 1/2001 | Leone-Bay et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,313,088 B1 | 11/2001 | Leone-Bay et al. |
| 6,344,213 B1 | 2/2002 | Leone-Bay et al. |
| 6,346,242 B1 | 2/2002 | Leone-Bay et al. |
| 6,348,207 B1 | 2/2002 | Milstein et al. |
| 6,358,504 B1 | 3/2002 | Leone-Bay et al. |
| 6,384,278 B1 | 5/2002 | Tang et al. |
| 6,391,303 B1 | 5/2002 | Haas et al. |
| 6,399,798 B2 | 6/2002 | Gschneidner et al. |
| 6,428,780 B2 | 8/2002 | Leone-Bay et al. |
| 6,440,929 B1 | 8/2002 | Milstein et al. |
| 6,461,643 B2 | 10/2002 | Milstein et al. |
| 6,525,020 B2 | 2/2003 | Leone-Bay et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,693,073 B2 | 2/2004 | Milstein et al. |
| 6,693,208 B2 | 2/2004 | Gscheidner et al. |
| 6,699,467 B2 | 3/2004 | Leone-Bay et al. |
| 2002/0001591 A1 | 1/2002 | Santiago et al. |
| 2002/0120009 A1 | 8/2002 | Leone-Bay et al. |

FOREIGN PATENT DOCUMENTS

| | | |
|---|---|---|
| EP | 0 036 145 A1 | 9/1981 |
| EP | 0036145 | 9/1981 |
| EP | 0 226 223 A1 | 6/1987 |
| EP | 226223 | 6/1987 |
| EP | 0 517 211 A1 | 9/1992 |
| EP | 0517211 | 9/1992 |
| EP | 576941 | 6/1993 |
| EP | 0 576 941 A1 | 1/1994 |
| EP | 0 007 979 | 5/2000 |
| ES | 369853 | 7/1989 |
| FR | 4446 A1 | 9/1966 |
| FR | 985.340 | 11/1966 |
| GB | 1 512 509 | 6/1978 |
| GB | 2095994 | 10/1982 |
| JP | 48-37819 A1 | 11/1973 |
| JP | 2 239 980 A1 | 9/1990 |
| JP | 02-239980 | 9/1990 |
| JP | 10507762 A | 7/1998 |
| JP | 2001 1513080 A | 8/2001 |
| JP | 2001 524109 A | 11/2001 |
| WO | WO-95/28838 A1 | 11/1995 |
| WO | WO-95/28920 A1 | 11/1995 |
| WO | WO-96/12473 A1 | 5/1996 |
| WO | WO-96/12474 A1 | 5/1996 |
| WO | WO-96/12475 A1 | 5/1996 |
| WO | WO-96/21464 A1 | 7/1996 |
| WO | WO-96/30036 A1 | 10/1996 |
| WO | WO-97/10197 A1 | 3/1997 |
| WO | WO-97/36480 A1 | 10/1997 |
| WO | WO-97/47270 A1 | 12/1997 |
| WO | WO-98/21951 A1 | 5/1998 |
| WO | WO-98/25589 A1 | 6/1998 |
| WO | WO-98/34632 A1 | 8/1998 |
| WO | WO-98/49135 | 11/1998 |
| WO | WO-98/50341 A1 | 11/1998 |
| WO | WO-99/16427 A1 | 4/1999 |
| WO | WO-99/29705 A1 | 6/1999 |
| WO | WO-00/06184 A1 | 2/2000 |
| WO | WO-00/07979 A1 | 2/2000 |
| WO | WO-00/08534 A1 | 2/2000 |
| WO | WO-00/07979 A2 | 5/2000 |
| WO | WO-00/40203 A1 | 7/2000 |
| WO | WO-00/46182 A1 | 8/2000 |
| WO | WO-00/48589 | 8/2000 |
| WO | WO-00/50386 A1 | 8/2000 |
| WO | WO-00/59480 A1 | 10/2000 |
| WO | WO-00/59863 | 10/2000 |
| WO | WO-01/32130 A1 | 5/2001 |
| WO | WO-01/32596 A1 | 5/2001 |
| WO | WO-01/44199 A1 | 6/2001 |
| WO | WO-01/51454 A1 | 7/2001 |
| WO | WO-01/70219 A1 | 9/2001 |
| WO | WO-01/92206 A1 | 12/2001 |
| WO | WO-02/19969 A1 | 3/2002 |
| WO | WO-02/069937 A1 | 9/2002 |
| WO | WO-02/070438 A1 | 9/2002 |
| WO | WO-02/100338 A1 | 12/2002 |
| WO | WO-03/026582 A1 | 4/2003 |
| WO | WO-03/045306 A1 | 6/2003 |
| WO | WO-03/057170 A1 | 7/2003 |
| WO | WO-03/057650 A1 | 7/2003 |

OTHER PUBLICATIONS

Picciola, G., "Synthesis Of Quinazolinone And Benzoxazainone Acids And Study Of Their Anti-Inflammatory Properties" IT, II Farmaco, Ed. Sc. vol. 31, No. 9 pp. 655-664—English Translation (1976).

Johansen, Marianne, et al. "Pro-Drugs As Drug Delivery Systems XIII. Kinetics Of Decomposition. Of N-Mannich Bases Of Salicylamide And Assessment Of Their Suitability As Possible Prodrugs for Amines" Int. J. Pharm. (1980), 7(2): 119-27 (1980).

Yusuke, Amino, et al. " Phenylalanine Derivatives Enhancing Intestinal Absorption of Insulin in Mice" Chem Pharm Bull 36 pgs. 4426-4434 (1988).

Brown, G. at al., "Receptor Binding Sites Of Hypoglycemic Sulfonylureas And Related[(Acylamino)Alkyl]Benzoic Acids" J Med Chem 27, 79-81 (1984).

Picciola, G., "Sintesi Di Acidi Chinazolinonici E Benzossazinonici E Studio Delle Loro Proprieta Antiinfiammatorie" IT, II Farmaco, Ed. Sc. vol. 31, No. 9 pp. 655-664 (1976).

Leone-Bay, A. "Acylated non-alpha-amino acids as novel agents for the oral delivery of heparin sodium, USP" Journal of Controlled Release 50: 41-49 (1998).

Leone-Bay, A., et al. "The evolution of an oral heparin dosing solution" Drugs of the Future vol. 22(8) 885-891 (1997).

Ho Koc-Kan, et al. "A Practical Synthesis of ☐-aminoalkanoic acid derivatives form Cycloalkanones" Synthetic Communication, vol. 26, No. 14: 2641-2649 (1996).

Leone-Bay, A., "N-Acylated alpha-amino acids as novel oral delivery agents for proteins"; Journal of Medicinal Chemistry vol. 38, 4263-4269 (1995).

Chem Abs. 73548-12-6 (Apr. 1991).

Chem Abs. 70204-54-5 (Apr. 1991).

Chem Abs. 184360-83-342 (1975) "Solubility and disassociation constants of some alicyclic acids".

Chemical Abstract, vol. 99, No. 23, Abst. No. 191473h (1983).

Riviera, Thersa M., et al., "Oral Delivery of Heparin in Combination with Sodium N-[8-S-hydroxybenzoyl] amino] caprylate: Pharmacological Considerations" Pharmaceutical Research vol. 14 (12) 1830-1834 (1997).

Brayden, D., et al., "Heprain Absorption across the intestine: Effects of Sodium N-[8-2hydroxybenzoy)Amino] Caprylate in rat in situ intestinal instillations and in Caco-2 monolayers", Pharmaceutical Research, 19971 vol. 14, No. 12, pp. 1772-1779.

Leone-Bay, Andrea, et al., "4-[4-[(2-Hydroxybenzoyl)amino]phenyl]butyric acid as a novel oral delivery agent for recombinant human growth hormone", Journal of Medicinal Chemistry, 1996, vol. 39, pp. 2571-2578.

Gurrieri and Siracusa, "Thermal Condensation of Some alpha-aminoacids with Phatalic Acid", Thermochimica Acta, 1973, vol. 7, pp. 231-239.

Leone-Bay, Andrea, et al., "Synthesis and Evaluation of Compounds that Facilitate the Gastrointestinal Absorption of Heparin", Journal of Medicinal Chemistry (1998) 41(7): 1163-1171.

Ho Koc-Kan, et al. "Solution Phase Preparation of Highly Pure Amide Mixtures Via In-Situ ChlorotrImethylsliane Protection and Activation" Synthetic Communication, vol. 27, No. 5: 883-895 (1997).

Palagiano, F., et al., "Synthesis, Stability And Anticonvulsant Activity Of Two New GABA Prodrugs" Pharmazle 52(4): 272-276 (1997).

Chem Abstract 70 (25), 1969, p. 311.

Emisphere Technologies Poster Presentation, "Oral Delivery of Human insulin in Diabetic Rats Using Novel Delivery Agents", Monica Carozza, et al., Nov. 16-19, 1988.

Leone-Bay, A. "Microsphere Formation in a Series of Derivatized Alpha-Amino Acids: Properties, Molecular Modeling, and Oral Delivery of Salmon Calcitonin"; Journal of Medicinal Chemistry vol. 38, 4257-4262 (1995).

Rivera, Theresa M., at al., "Oral Delivery of Heparin in Combination with Sodium in N-[8-2-Hydroxybenzoyi)Amino)Caprylate: Pharmacological Considerations", Pharmaceutical Research, 1997, vol. 14, No. 12, pp. 1830-1834.

O'Shaughnessy, Catherine, et al., "Acylated Non-Alpha Amino Acids Increase the Permeation of Recombinant Human Growth Hormone Through CACO-2 Monolayers", Abstract 1997 AAPS Annual Meeting, Nov. 1997.

O'Shaughnessy, Catherine, "Acylated Non-Alpha Amino Acids Increase the Permeation of Recombinant Human Growth Hormone Through CACO-2 Monolayers", Poster Presentation at 1997 AAPS Annual Meeting, Nov. 1997.

O'Shaughnessy, Catherine, et al, "Acylated Non-Alpha Amino Acids Increase the Permeation of Horseradish Peroxidase Through CACO-2 Monolayers", Abstract 1997 AAPS Annual Meeting, Nov. 1998.

Freeman, John, et al., "The Use of Parallel Synthesis to Prepare Compounds For An In Vivo Assay", Poster Presentation at 217th American Chemical Society Meeting, Mar. 21, 1999.

Freeman, John, et al., "The Use of Parallel Synthesis to Prepare Compounds For An In Vivo Assay", Abstract, 217th American Chemical Society Meeting, Mar. 21, 1999.

O'Toole, Doris, et al., "Increased Throughput in an In Vivo Assay by Use of Parallel Synthesis Array" Abstract 1998 AAPS Annual Meeting Abstracts, Nov. 1998.

O'Toole, Doris, et al., "Increased Throughput in an In Vivo Assay by Use of Parallel Synthesis Array", Poster Presentation at 1998 AAPS Annual Meeting, Anaheim, California, Nov. 16, 1998.

Leone-Bay, Andrea, et al., "Oral Delivery of Biologically Active Parathyroid Hormone", Pharmaceutical Research. 2001, vol. 18, No. 7, pp. 964-970.

Yalcin at al., Synthesis and Microbiological Activity of some Novel N-(2-Hydroxyl-5-substituted Phenyl) Benzacetamides, Phenoxyacetamides and Thiophenoxyacetamides. Il Farmaco, 1997, vol. 52, No. 11, pp. 685-689, especially p. 686, compound 5a-k and p. 687, Table 1.

Charbon, Vinciane, et al., "Targeting of Drug to the Hepatocytes by Fatty Acids. Influence of the Carrier (Albumin or Galactosylated Albumin) on the Fate of the Fatty Acids and their Analogs," Pharmaceutical Research, vol. 13, No. 1, 1996, p. 27-31.

Kondo, Kazuhiko, et al., "Studies on Biologically Active Nucleosides and Nucleotides. 5. Synthesis and Antitumor Activity of Some 2,2'-Anhydro-1-(3',5-di-$O$-acyl-$\beta$-D-arabinofuranosyl)cytosine Salts and 2,2'-Anhydro-1-(3'-$O$-acyl-$\beta$-D-arabinofuranosyl)cytosine 5'-Phosphates," Journal of Medicinal Chemistry, vol. 22, No. 6, 1979, p. 639-646.

Schlosstein, Lee, et al., "Studies with Some Novel Uricosuric Agents and Their Metabolites: Correlation between Clinical Activity and Drug-Induced Displacement of Urate from its Albumin-Binding Sites," Journal of Laboratory and Clinical Medicine, vol. 82, No. 3, 1973, p. 412-418.

COMPOUNDS AND COMPOSITIONS FOR DELIVERING ACTIVE AGENTS

This is a continuation of U.S. Ser. No. 11/173,075 filed Jun. 30, 2005, now allowed, which is a divisional of U.S. Ser. No. 09/762,067 filed Aug. 3, 2001, which is a continuation of International Application No. PCT/US99/17974 filed Aug. 6, 1999 and claims benefit of U.S. Ser. No. 60/095,778 filed Aug. 7, 1998, U.S. Ser. No. 60/098,500 filed Aug. 31, 1998, U.S. Ser. No. 60/108,366 filed Nov. 13, 1998 and U.S. Ser. No. 60/119,207 filed Feb. 5, 1999.

FIELD OF THE INVENTION

The present invention relates to compounds for delivering active agents, such as biologically or chemically active agents, to a target. These compounds are well suited for forming non-covalent mixtures with active agents for oral, intracolonic, or other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere compounds as well as methods for their preparation and use. These proteinoid microspheres are useful for the delivery of a number of active agents. In addition, certain modified amino acids have been used to deliver pharmaceuticals. See, e.g., U.S. Pat. No. 5,629,020; U.S. Pat. No. 5,643,957; U.S. Pat. No. 5,650,386; and U.S. Pat. No. 5,776,888.

However, there is still a need for simple, inexpensive delivery systems which are easily prepared and which can deliver a broad range of active agents by various routes.

SUMMARY OF THE INVENTION

Compounds and compositions which are useful in the delivery of active agents are provided. The compounds comprise the following compounds or salts thereof.

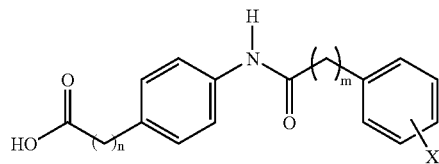

| Cpd. # | n | m | X |
|---|---|---|---|
| 1 | 3 | CH$_2$O | 2-OH |
| 2 | 3 | CH$_2$O | 4-OH |
| 3 | 3 | 0 | 2-NH$_2$, 5-F |
| 4 | 2 | 0 | 2-NH$_2$, 5-F |
| 5 | 3 | 0 | 2-NH$_2$, 5-Cl |
| 6 | 2 | 0 | 2-NH$_2$, 3,5-Cl |
| 7 | 2 | 0 | 2-NHMe |
| 8 | 3 | 1 | 4-OH |
| 9 | 3 | 1 | 3-OH |
| 10 | 3 | 0 | 2-NHMe |
| 11 | 2 | 0 | 2-OH, 3-F; 5-Cl |
| 12 | 2 | 0 | 2-OH, 3-Cl; 5-F |
| 13 | 2 | 0 | 2-OH, 3,5-Me |
| 14 | 3 | 0 | 2-OH, 3,5-Me |
| 15 | 2 | 0 | 2-OH, 3-Br, 5-Cl |
| 16 | 3 | 2 | 2-OH |
| 17 | 2 | 2 | 2-OH |
| 18 | 2 | 0 | 2-OH, 3,5-F |
| 19 | 3 | 0 | 2-OH, 3,5-F |
| 20 | 2 | 0 | 2-OH, 5-F |
| 21 | 3 | 0 | 2-OH, 5-F |
| 22 | 2 | 0 | 2-NHAc |
| 23 | 3 | 0 | 2-SO$_3$Na |
| 24 | 3 | 0 | 2-OH, 3-Me, 5-F |
| 25 | 3 | 0 | 2-OH, 3-Me, 5-Cl |
| 104 | 3 | 0 | 2-OH, 4-Ome |
| 133 | 2 | 0 | 2-OH, 3-Me, 5-Cl |

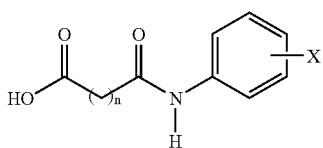

| Cpd # | n | X |
| --- | --- | --- |
| 26 | 7 | 2-OH, 5-Me |
| 27 | 6 | 2-OH |
| 28 | 8 | 2-OH, 3,5-Cl |
| 29 | 7 | 2-OH, 3,5-Cl |
| 30 | 8 | 2-OH, 4-Me |
| 31 | 7 | 2-CH$_2$OH |
| 32 | 4 | 2-OH, 4-Me |
| 33 | 7 | 2-OH, 4-Me |
| 34 | 7 | 2-OH, 5-F |
| 35 | 8 | 2-OH, 5-F |
| 119 | 3 | 2-OH, 5-Cl |
| 120 | 5 | 2-OH, 5-Cl |
| 121 | 6 | 2-OH, 5-Cl |
| 122 | 7 | 2-OH, 5-Cl |
| 123 | 8 | 2-OH, 5-Cl |
| 124 | 1 | 2-OH, 5-Cl |
| 125 | 2 | 2-OH, 5-Cl |
| 126 | 4 | 2-OH, 5-Cl |
| 127 | 9 | 2-OH, 5-Cl |
| 128 | 10 | 2-OH, 5-Cl |
| 129 | 11 | 2-OH, 5-Cl |
| 130 | 12 | 2-OH, 5-Cl |
| 131 | 7 | 2-OH, 3,4-F |
| 132 | 7 | 2-OH, 4-F |

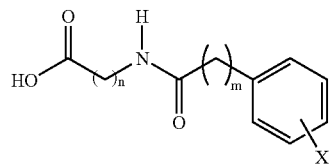

| Cpd # | n | m | X |
| --- | --- | --- | --- |
| 95 | 11 | 0 | 2-CH$_3$ |
| 96 | 11 | 0 | 2-OCH$_3$ |
| 97 | 11 | 0 | 2-F |
| 98 | 11 | 0 | H |
| 99 | 9 | 0 | 2-CH$_3$ |
| 100 | 9 | 0 | H |
| 101 | 5 | 0 | 2-CH$_3$ |
| 102 | 1 | 0 | 2-OH, 4-OMe |
| 103 | 2 | 0 | 2-OH |
| 105 | 3 | 0 | 2-OH, 5-Cl |
| 106 | 3 | 0 | 2-OH, 4-OMe |
| 107 | 5 | 0 | 2-OH, 4-OMe |
| 108 | 9 | 0 | 2-OH, 4-OMe |
| 109 | 11 | 0 | 2-OH, 4-OMe |
| 110 | 1 | 0 | H |
| 111 | 1 | 0 | 2-CH$_3$ |
| 112 | 1 | 0 | 2-OMe |
| 113 | 1 | 0 | 2-F |
| 114 | 1 | 0 | 2-OH, 5-Cl |
| 116 | 4 | 0 | 2-OH, 5-Cl |
| 117 | 5 | 0 | 2-OH, 5-Cl |
| 118 | 6 | 0 | 2-OH, 5-Cl |

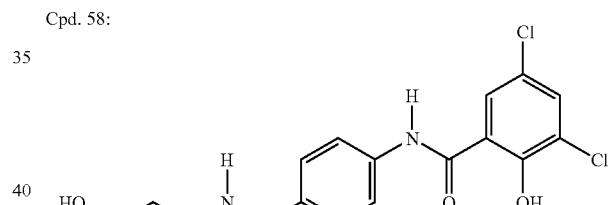

| Cpd # | n | m | X |
| --- | --- | --- | --- |
| 36 | 7 | 0 | 2-OH, 3-NH$_2$, 5-NO$_2$ |
| 37 | 5 | 0 | 2-OH, 4-Cl |
| 38 | 7 | CH$_2$O | 4-OH |
| 39 | 7 | 0 | 2-NH$_2$, 5-F |
| 40 | 7 | 0 | 2-NH$_2$, 5-Cl |
| 41 | 7 | 0 | 2-OH, 3,5-F |
| 42 | 7 | 0 | 2-OH, 3,4-F |
| 43 | 7 | 0 | 2-NHMe |
| 44 | 7 | 0 | 2-OH, 4-F |
| 45 | 7 | 0 | 2-OH, 3-F, 5-Cl |
| 46 | 7 | 1 | 4-OH |
| 47 | 7 | 0 | 2-OH, 3-Cl, 5-F |
| 48 | 7 | 0 | 2-OH, 3-Br, 5-Cl |
| 49 | 7 | 0 | 2-OH, 3,5-Me |
| 50 | 7 | 0 | 2-OMe, 6-Cl |
| 51 | 7 | 0 | 2-OH, 6-Cl |
| 52 | 7 | 1 | 3-OH |
| 53 | 7 | 2 | 2-OH |
| 54 | 7 | 0 | 2-OH, 5-F |
| 55 | 7 | 0 | 2-OH, 3-Me, 5-Cl |
| 56 | 7 | 0 | 2-OH, 3-Me, 5-F |
| 57 | 9 | 0 | 2-OH, 5-Cl |
| 85 | 9 | 0 | 2-F |
| 86 | 5 | 0 | 2-F |
| 87 | 10 | 0 | H |
| 88 | 10 | 0 | 2-F |
| 89 | 5 | 0 | H |
| 90 | 3 | 0 | 2-OCH$_3$ |
| 91 | 3 | 0 | 2-CH$_3$ |
| 92 | 3 | 0 | 2-F |
| 93 | 3 | 0 | H |
| 94 | 9 | 0 | 2-OCH$_3$ |

Cpd. 58:

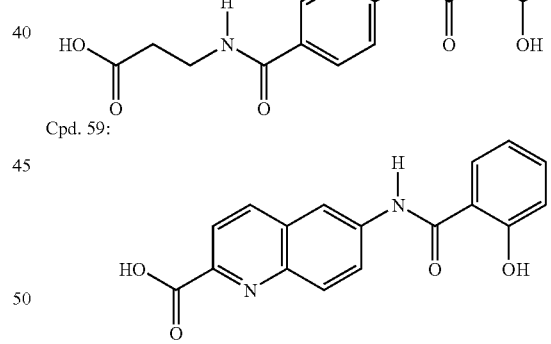

Cpd. 59:

Cpd. 60: X = F
Cpd. 61: X = OH

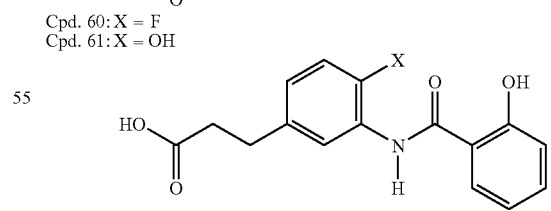

Cpd. 62: X = SO
Cpd. 63: X = SO$_2$

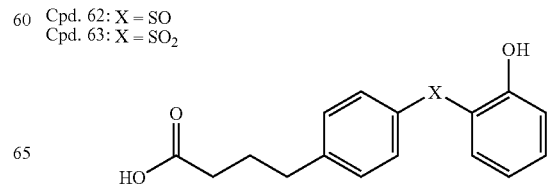

Cpd. 64
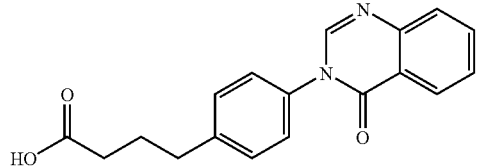
Cpd. 65: X = Cl; Y = OMe
Cpd. 66: X = F; Y = OH
Cpd. 67: X = F; Y = OMe
Cpd. 68: X = OMe; Y = OH
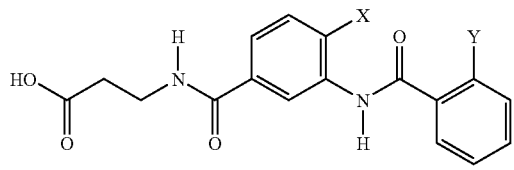
Cpd. 69: n = 1
Cpd. 70: n = 2
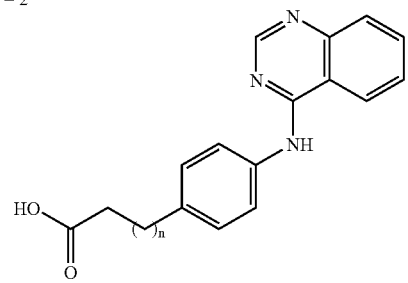
Cpd. 71:
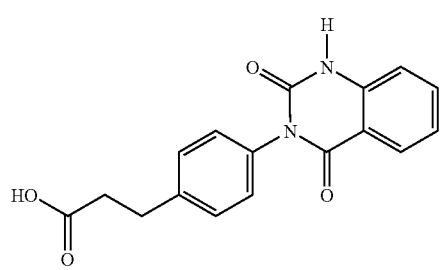
Cpd. 72:
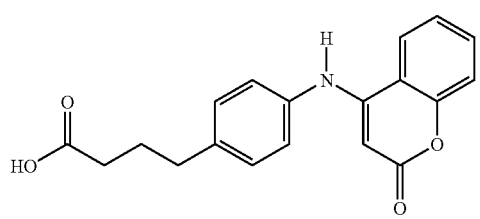
Cpd. 73:
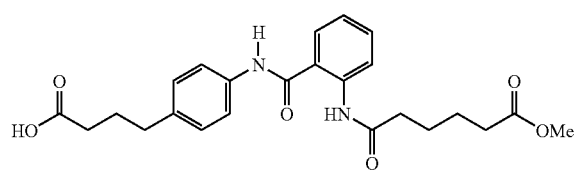
Cpd. 74: X = Me
Cpd. 75: X = OMe
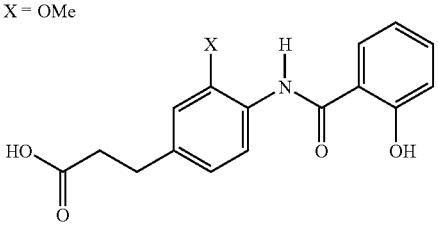
Cpd. 76: X = Y = OMe; Z = H; n = 1
Cpd. 77: X = OH; Y = Z = Cl; n = 1
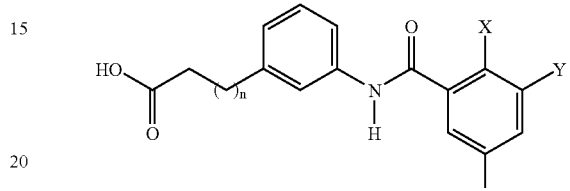
Cpd. 78: n = 2
Cpd. 134: n = 3
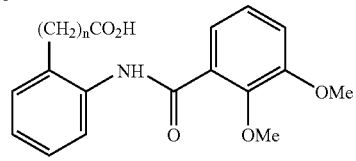
Cpd. 79:
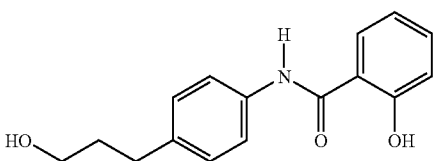
Cpd. 80:
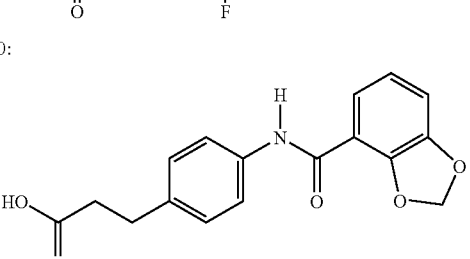
Cpd. 81:
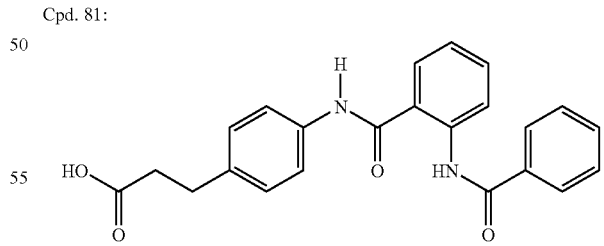
Cpd. 82:
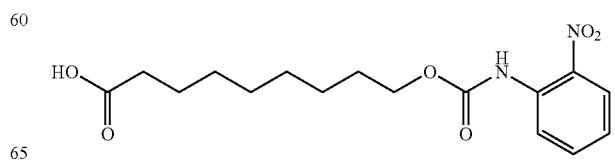

Cpd. 83:

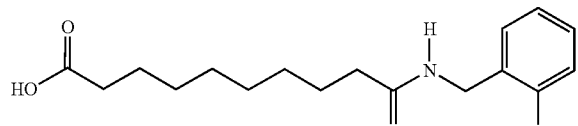

Cpd. 84: R = C(O)—NH—(CH$_2$)$_7$COOH
Cpd. 135: R = (CH$_2$)$_7$COOH

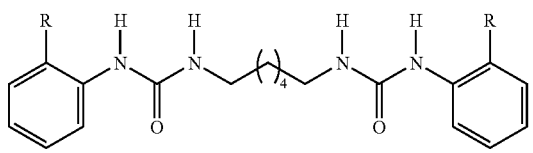

The compositions of the present invention comprise at least one active agent, preferably a biologically or chemically active agent, and at least one of the compounds, or salts thereof, of the present invention. Methods for the preparation and administration of such compositions are also provided. The compositions comprising the compounds and active agents have utility in the delivery of active agents to selected biological systems and in an increased or improved bioavailability of the active agent compared to administration of the active agent alone.

DETAILED DESCRIPTION OF THE INVENTION

The compositions of the present invention include an active agent and a delivery agent. These compositions may be used to deliver various active agents through various biological, chemical, and physical barriers and are particularly suited for delivering active agents which are subject to environmental degradation.

Other advantages of the present invention include the use of easy to prepare, inexpensive raw materials. The compositions and the formulation methods of the present invention are cost effective, simple to perform, and amenable to industrial scale up for commercial production.

Compounds

The compounds may be in the form of the carboxylic acid and/or their salts. Salts include but are not limited to organic or inorganic salts, such as sodium salts. In addition, poly amino acids and peptides comprising one or more of these compound may be used.

An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. See *Chambers Biological Dictionary*, editor Peter M. B. Walker, Cambridge, England: Chambers Cambridge, 1989, page 215. One or more of the amino acids or peptide units may be acylated or sulfonated.

Many of the compounds described herein may be derived from amino acids and can be readily prepared from amino acids by methods within the skill of those in the art based upon the present disclosure and the methods described in WO96/30036, WO97/36480, U.S. Pat. No. 5,643,957 and U.S. Pat. No. 5,650,386. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, N.Y. (1981), the disclosure of which is hereby incorporated herein by reference.

The compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones, and particularly hormones which by themselves do not pass (or which pass only a fraction of the administered dose) through the gastro-intestinal mucosa and/or are susceptible to chemical cleavage by acids and enzymes in the gastro-intestinal tract; polysaccharides, and particularly mixtures of mucopolysaccharides; carbohydrates; lipids; other organic compounds; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including α, β and γ; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; analogs, fragments, mimetics or polyethylene glycol (PEG)-modified derivatives of these compounds; or any combination thereof.

Delivery Systems

The compositions of the present invention comprise a delivery agent and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration.

The administration mixtures may be prepared by mixing an aqueous solution of the compound with an aqueous solution of the active ingredient, just prior to administration. Alternatively, the compound and the biologically or chemically active ingredient can be admixed during the manufacturing process.

The solutions may optionally contain additives such as phosphate buffer salts, citric acid, glycols, or other dispersing agents. Stabilizing additives may be incorporated into the solution, preferably at a concentration ranging between about 0.1 and 20% (w/v).

The delivery compositions of the present invention may also include one or more enzyme inhibitors. Such enzyme inhibitors include, but are not limited to, compounds such as actinonin or epiactinonin and derivatives thereof. Derivatives of these compounds are disclosed in U.S. Pat. No. 5,206,384. Other enzyme inhibitors include, but are not limited to, aprotinin (Trasylol) and Bowman-Birk inhibitor.

The amount of active agent is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form, such as a capsule, a tablet, a powder, or a liquid, because the dosage unit form may contain a plurality of compound/biologically or chemically active agent compositions or may contain a divided pharmacologically, biologically, therapeutically, or chemically effective amount. The total effective amount can then be administered in cumulative units containing, in total, pharmacologically, biologically, therapeutically or chemically active amounts of biologically or pharmacologically active agent.

The total amount of active agent to be used can be determined by methods known to those skilled in the art. However, because the compositions may deliver active agents more efficiently than prior compositions, lower amounts of biologically or chemically active agents than those used in prior dosage unit forms or delivery systems can be administered to the subject, while still achieving the same blood levels and/or therapeutic effects.

The presently disclosed compounds deliver biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as cows, pigs, dogs, cats, primates; and particularly humans; and insects. The system is particularly advantageous for delivering chemically or biologically active agents which would otherwise be destroyed or rendered less effective by conditions encountered before the active agent reaches its target zone (i.e. the area in which the active agent of the delivery composition is to be released) and within the body of the animal to which they are administered. The compounds and compositions of the present invention are also useful in administering active agents, especially those which are not ordinarily deliverable by a particular route, especially by the oral route, or those for which improved delivery is desired. Delivery can be improved by delivering more active agent over a period of time, or in a particular time period (such as to effect quicker delivery).

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Example 1

Compound Preparation

Method A: Preparation of compound 26. A 1 L round bottom flask fitted with a magnetic stirrer was charged with 2-amino-p-cresol (1.71 g, 13.88 mmol, 1 equiv.) and 2M aqueous sodium hydroxide (20 ml). Methyl azeloyl chloride (3.08 g, 13.96 mmol, 1.01 eq.) Was added dropwise to the stirred solution at 0 C. After the addition, the reaction mixture was allowed to warm to ambient temperature and was stirred for 4-5 hours at ambient temperature. The pH of the solution was kept at about 11-12 by the addition of 20% sodium hydroxide. The solution was then extracted with ethyl acetate (3×30 ml). Combined organic layers were dried over sodium sulfate, filtered and concentrated in vacuo. The residue was redissolved in THF (50 ml) and treated with 2N NaOH (20 ml). The resulting mixture was stirred at room temperature for 8 hours. TLC indicated the reaction was complete. The mixture was concentrated in vacuo and acidified. The resulting solid was collected, recrystallized with methanol/acetone/water to afford 2.5 g of product.

Compounds 11-15, 18-21, 24, 25, 27-35, 48-50, 54-56, 58, 65-68, 73, 83, 110, 120 and 131-133 were also prepared by this method using the appropriate starting materials. Compounds 120, 122 and 123 were also prepared by this method using the appropriate starting materials, except that the reaction was run containing the THF.

Method B: Preparation of compound 60. A slurry of 1.03 g (5.62 mmol) of 3-amino-4-fluorohydrocinnamic acid and 20 ml of methylene chloride was treated with 1.45 ml (1.24 g, 11.4 mmol) of trimethylsilyl chloride and was heated to reflux for 150 min. The reaction mixture was cooled to 0 C and treated with 2.4 ml (1.74 g, 17.2 mmol) of triethylamine. After stirring for 5 min, this mixture was poured into an addition funnel and added slowly to a 0 C solution of 1.21 g (6.09 mmol) of O-acetylsalicyloyl chloride and 10 ml of methylene chloride. The reaction mixture was warmed to 25 C and stirred for 18 hr. Washing with 3% aqueous hydrochloric acid (2×20 ml), water (1×20 ml) and brine (1×15 ml), drying over sodium sulfate, and concentration in vacuo gave a brownish yellow solid. The solid was recrystallized from 15 ml of 65% ethanol/water to give a brown solid. The solid was dissolved in saturated aqueous sodium bicarbonate solution. After stirring until the acetate was cleaved off (by HPLC), the solution was acidified, causing a precipitate to develop. Isolation by filtration afforded 0.58 g of (38% yield) of product, mp=202-4 C.

Compounds 59, 61, 74-81, 107, 109 and 111-113 were also prepared by this method using the appropriate starting materials. Compounds 37, 42, 44 and 134 could also be prepared by this method using the appropriate starting materials.

Method C: Preparation of compound 1. 1,4-benzodioxan-2-one (4.50 g, 30 mmol) was dissolved in acetonitrile (75 ml) in a 250 ml round bottom flask equipped with a magnetic stir bar, argon purge and cold-water condenser. Triethylamine (4.17 ml, 3.03 g, 30 mmol) and 4-(4-aminophenyl)butyric acid (5.37 g, 30 mmol) were added. The reaction mixture was heated to reflux for 2 hr, stirred overnight at 25 C and concentrated in vacuo. The brown residue was taken up in methylene chloride, and washed with aqueous 1N hydrochloric acid solution (1×100 ml). The solid that formed was isolated by filtration, and rinsed with aqueous 1N hydrochloric acid solution and water. The resulting solid was dried overnight in a vacuum oven, yielding the compound as a tan solid (9.19 g, 93% yield).

Compound 53 was made by this method starting from dihydrocoumarin and 8-aminocaprylic acid.

Method D: Preparation of compound 36. 8-(N-3,5-dinitrosalicyloyl)aminocaprylic acid was prepared using Method T starting from 3,5-dinitrosalicylic acid and 8-aminocaprylicacid.

A solution of 0.7 g (1.9 mmol) of 8-(N-3,5-dinitrosalicyloyl)aminocaprylic acid and 40 ml of ethyl acetate was treated with 70 mg of 10% Pd/C and was placed under a hydrogen atmosphere for 18 hr. The catalyst was removed by filtration. The filtration was concentrated in vacuo. The residue was recrystallized from methanol/acetone/water to afford 0.4 g of (62% yield) of product, mp=156-7 C.

Method E: Preparation of compound 2. 4-(4-(4-benzyloxyphenoxyacetyl)amino)phenyl)butyric acid was prepared by the reaction of 4-(4-aminophenyl)butyric acid with 4-benzyloxyphenoxyacetyl chloride using Method C.

A slurry of 5.00 g (11.9 mmol) of 4-(4-(4-benzyloxyphenoxyacetyl)amino)phenyl)butyric acid and 150 ml methyl alcohol was stirred under argon for approximately 20 minutes. A catalytic amount (0.4 g) of 10% palladium on carbon was added in one portion. The reaction vessel was evacuated. The reaction was kept under a hydrogen atmosphere overnight at room temperature. The palladium on carbon was then filtered off and the filtrate was concentrated under vacuum to give the product as a white solid.

Compounds 8, 9 and 38 were also prepared by this method using the appropriate starting materials.

Method F: Preparation of compound 39. A suspension of 10.82 g (59.7 mmol) of 5-fluoroisatoic anhydride, 9.50 g of 8-aminocaprylic acid, 16.8 g of 50 wt % $K_2CO_3$/water and 40 ml of dioxane was heated to reflux. After 2 hr, the reaction was complete (as measured by HPLC). The deep purple solution was cooled to 25 C and acidified with 3% aqueous hydrochloric acid to pH=4.00, causing a dark precipitate to form. The solid was isolated by filtration and recrystallized from 65% ethanol/water to give 11.86 g (67% yield) of the product as a yellow solid, mp=108-9 C.

Compounds 3-7, 10, 40 and 43 were also prepared by this method using the appropriate starting materials.

Method G: Preparation of compound 62. A 5 C mixture of 4-(4-aminophenyl)butyric acid (1.0 eq) and aqueous 6N hydrochloric acid (5.44 eq) was treated with 1.05 eq of a 3N aqueous solution of sodium nitrite, adding slowly so as to keep the temperature below 5 C. A solution of 2.8N aqueous potassium iodide (1.01 eq) was added. The reaction was stirred overnight. The layers were separated. The organic phase was purified by flash chromatography using methanol/methylene chloride as eluant to give 4-(4-iodophenyl)butyric acid.

A solution of 4-(4-iodophenyl)butyric acid (0.86M) and dimethylformamide was treated with 2 eq of potassium carbonate, 1.5 eq of 2-hydroxythiophenol and a catalytic amount of cuperic acetate (0.01 eq). The reaction mixture was refluxed for 18 hr, cooled to 25 C, acidified with aqueous acid and extracted with ethyl acetate. The organic phase was concentrated. The residue was purified by flash chromatography using ethyl acetate/hexane as eluant to give 4-(4-(2-hydroxyphenyl)thiophenyl)butyric acid.

A 0.33M solution of 4-(4-(2-hydroxyphenyl)thiophenyl) butyric acid and ethyl acetate/acetic acid was treated with a 9.8M aqueous solution of hydrogen peroxide. After stirring for 12 hr, the layers were separated. The organic phase was concentrated. Purification of the residue by flash chromatography using toluene/acetone/hexane as eluant gave the product.

Method H: Preparation of compound 82. A 0 C solution of 3.97 g (17.8 mmol) of 9-bromo-1-nonanol and methylene chloride was treated with a solution of 2.91 g of 2-nitrophenylisocyanate and 10 ml of methylene chloride. The reaction mixture was heated to reflux for 2 hr, stirred at 25 C for 16 hr and concentrated in vacuo. The yellow solid was identified as 9-bromononyl N-(2-nitrophenyl)carbamate and was used as is.

A suspension of 2.99 g (7.72 mmol) of 9-bromononyl N-(2-nitrophenyl)carbamate, 1.61 g (23.3 mmol) of sodium nitrite, 4.50 ml (4.72 g, 78.5 mmol) of acetic acid and 15 mL of dimethylsulfoxide was stirred at 35 C for 7 hr. The reaction mixture was acidified with 3% aqueous hydrochloric acid and extracted with diethyl ether (3×20 ml). The combined organic layers were extracted with 2N aqueous sodium hydroxide solution (3×20 ml). The basic aqueous phases were acidified with 3% aqueous hydrochloric acid, causing a precipitate to develop. The solid was collected by filtration to give 0.79 g (30% yield) of compound, mp=90-1 C.

Method I: Preparation of compound 64. 4-(4-(2-aminobenzoyl)aminophenyl)butyric acid was prepared using Method F starting from isatoic anhydride and 4-(4aminophenyl)butyric acid.

A slurry of 4.73 g (16.0 mmole) 4-(4-(2-aminobenzoyl) aminophenyl)butyric acid and 40 ml of triethylorthoformate was placed under an argon atmosphere and heated to reflux for 18 hours. The reaction became clearer during the reflux. The reaction mixture was cooled to room temperature and the resulting solid was collected by filtration to give 4.47 g (88% yield) of the product, mp=201-204 C.

Method J: Preparation of compound 63. A 0.05M solution of 4-(4-(2-hydroxyphenyl)thiophenyl)butyric acid in methylene chloride was treated with 4 eq of m-chloroperbenzoic acid at 0 C. The reaction mixture was allowed to warm to 25 C and stirred for 12 hr. The solvent was stripped off. The residue was purified by flash chromatography using ethyl acetate/hexane/acetic acid as eluant to give the product.

Method K: Preparation of compound 84. 8-N-(2-aminobenzoyl)aminocaprylic acid was prepared using Method F, starting from isatoic anhydride and 8-aminocaprylic acid.

A slurry of 6.88 g (24.7 mmol) of 8-N-(2-aminobenzoyl) aminocaprylic acid and 100 mL of methylene chloride was cooled to 0 C and treated with a solution of 2.00 ml (2.08 g, 12.4 mmol) of hexamethylenediisocyanate and 5 ml of methylene chloride. The reaction mixture was heated to reflux for 2 hr, cooled to 25 C and diluted with 20 ml of ethanol. The resulting solid was isolated by filtration and recrystallized from 1/2/1 ethyl acetate/ethanol/water, yielding a total of 5.15 g (57% yield) of the product as a tan solid, mp=138-142 C.

Compound 135 could also be prepared by this method using the appropriate starting materials.

Method L: Preparation of compound 51. 8-(N-6-chloro-2-methoxybenzoyl)aminocaprylic acid was prepared using Method A, starting from 2-chloro-6-methoxybenzoic acid and 8-aminocaprylic acid.

A suspension of 1.27 g (3.72 mmol) of 8-(N-6-chloro-2-methoxybenzoyl)aminocaprylic acid in 200 ml of methylene chloride under an argon atmosphere was cooled to 0 C and treated with 8 ml of a 1.0 M boron tribromide solution in methylene chloride. After stirring for 60 min, TLC indicated that the reaction was complete. The reaction mixture was quenched with water and stirred for 30 min. The layers were separated. The aqueous layer was extracted with methylene chloride (2×30 ml). The combined organic layers were dried over sodium sulfate, filtered and concentrated in vacuo. The resulting white-solid was recrystallized from methanol/acetone/water to afford 0.5 g (43% yield) of product, mp=156-7 C.

Method M: Preparation of compound 17. A solution of 4.28 mL (0.034 mole) of dihydrocoumarin, 75 ml of acetonitrile, 4.79 ml of triethylamine (3.48 g, 0.0343 mole), and 5.62 g of 3-(4-aminophenyl)propionic acid (0.034 mole) was stirred under argon and the flask heated to reflux for 18 hours. The reaction was cooled to room temperature, and the acetonitrile removed under vacuum. The residue was stirred in methylene chloride and 1N aqueous hydrochloric acid, forming a white solid. The solid was filtered off, rinsed with water and methylene chloride, then vacuum dried at 50 C to give 9.17 g (86.1% yield) of product, mp=163-165 C.

Compound 16 was also prepared by this procedure using the appropriate starting materials.

Method N: Preparation of compound 52. A solution of 10.0 g (65.8 mmol) of 3-hydroxyphenylacetic acid in 50 ml xylenes was treated with 6.45 ml (68.4 mmol) acetic anhydride. This mixture was refluxed for about 2.5 hours until most of the xylenes and acetic acid by-product was distilled off. The oligo-(3-hydroxyphenylacetic acid) was isolated as a brown oil.

This oil was dissolved in 150 ml of 1,4-dioxane. A solution of 9.97 g (62.7 mmol) of 8-aminocaprylic acid and 34.5 ml of 2N NaOH solution was added to the oligomer solution. The reaction mixture was heated to reflux overnight. The dioxane was then removed under vacuum. The brown residue was taken up in 2N NaOH and extracted with two 100 ml portions of ethyl acetate. The aqueous layer was then acidified with 2N sulfuric acid solution and was then extracted with three 100 ml portions of ethyl acetate. The combined ethyl acetates layers were decolorized with activated carbon, dried with sodium sulfate, and concentrated under vacuum. The resulting brown oil was then purified by column chromatography using a silica gel column with ethyl acetate:hexane:acetic acid (60:40:1) as the mobile phase. The resulting white solid was washed with warm water (40-50 C) to give the product as a white solid.

Compounds 41, 45 and 47 were also prepared by this method using the appropriate starting materials.

Method O: Preparation of compound 22. A solution of 3.0 g (11.0 mmol) of 3(-4-(2 aminobenzoyl)aminophenyl)propionic and 10 ml of methylene chloride. Acetic anhydride (1.12 g, 1.04 ml, 11.0 mmol) was added dropwise over 30 minutes. Once the acetic anhydride was all added, the reaction was stirred at room temperature for 18 hr. The reaction was complete as determined by HPLC. The resulting solid was isolated by filtration. The resulting white solid was dried in a vacuum oven overnight yielding the product.

Method P: Preparation of compound 23. A mixture of 5.13 g (27.9 mmol) of 2-sulfobenzoic cyclic anhydride, 5.0 g (27.9 mmol) of 4-(4-aminophenyl)butyric acid and 100 ml of acetonitrile was stirred for 18 hr. The milky solution was concentrated. The residue was taken up into 50 ml of cold aqueous hydrochloric acid, extracted with ethyl acetate (5×50 ml) and concentrated. The residue was purified by column chromatography using acetonitrile as the eluant to give the product.

Method Q: Preparation of compound 57. A solution of 10 g of 5-chloro-2-hydroxybenzamide (58.0 mmol), pyridine (22 ml) and acetonitrile (25 ml) was stirred in an ice bath. Ethyl chloroformate (6.1 ml, 0.0638 mol) was added dropwise. The pink solution was stirred for 30 minutes at <10° C. The ice bath was replaced with an oil bath. The reaction mixture was heated to 95° C. and the volatiles were distilled off (43 ml). The reaction was cooled to room temperature, causing a white solid to form. The mixture was poured into water (100 ml) and acidified with concentrated aqueous hydrochloric acid. The resulting solid was filtered and recrystallized in hot ethanol to give 9.77 g of 6-chloro-2H-1,3-benzoxazine-2,4(3H)-dione.

A slurry of 9.77 g of 6-chloro-2H-1,3-benzoxazine-2,4 (3H)-dione (50 mmol) and 60 ml of DMF was treated with a solution of 1,10-dibromodecane (52.52 g, 0.175 mol) and DMF (60 ml) was added. Diisopropylethylamine (9.6 ml, 55 mmol) was added dropwise. A thermometer and condenser were attached, and the flask was placed in an oil bath. The reaction was heated to 60 C for approximately 3 hrs, cooled to 47 C and hexanes (150 ml) were added. The mixture was diluted with water (175 ml). The resulting solids were removed by filtration. The aqueous layer was washed with warm hexanes. The resulting solids were filtered from the hexane layer and recrystallized from warm hexanes to give 10.39 g of 6-chloro-3-(10-bromodecyl)-2H-1,3-benzoxazine-2,4(3H)-dione.

A mixture of 6-chloro-3-(10-bromodecyl)-2H-1,3-benzoxazine-2,4(3H)-dione (10.39 g, 0.025 mol), sodium nitrite (5.52 g, 0.08 mol) and DMSO (60 ml) were stirred under argon. Acetic acid (14.9 ml) was added and the reaction was heated to 75 C for 6 hrs. After being cooled to room temperature, the reaction mixture was then dissolved in ethyl acetate and washed with 0.5N HCl (2×) and 2N NaOH (2×) The sodium hydroxide layers were stirred for 2 hrs and 20 minutes, and the solution was acidified with 2M $H_2SO_4$. The solids were then filtered and recrystallized from methylene chloride and hexanes. Yield: 3.0 g.

Method R. Preparation of compound 71. A solution of 3.22 g (18.4 mmol) of mono-methyl phthalate, 2.90 ml (2.11 g, 20.8 mmol) of triethylamine and 20 ml of acetone was cooled in an ice (salt) bath and treated with a solution of 2.00 ml (2.27 g, 20.9 mmol) of ethyl chloroformate and 10 ml of acetone, added dropwise over 20 min. The white cloudy solution was stirred for 15 min and treated with a solution of 2.53 g (38.9 mmol) of sodium azide and 8 ml of water. After stirring for 30 min the still cloudy solution was poured into 50 ml of ice water and extracted with toluene (3×30 ml). The toluene phase was dried over sodium sulfate and heated to reflux for 80 min. The reaction mixture was cooled to 0 C. In several portions, 3.11 g (18.8 mmol) of 3-(4-aminophenyl)propionic acid was added over 5 min. After stirring for 64 hr, the reaction mixture was diluted with 80 ml of a 3:1 dioxane/water solution and heated to reflux for 3 hr. The cooled mixture was extracted with 2N (1×30 ml) and 0.5N (2×30 ml) sodium hydroxide. The combined aqueous layers were acidified, causing a white solid to form. Isolation by filtration, dissolution in ethyl acetate, filtration of the insoluble material and concentration of the filtrate gave 1.13 g of solid product.

Method S. Preparation of compound 69. A slurry of 3.17 g 21.7 mmol) of 4-hydroxyquinoazoline, 3 drops of dimethylformamide and 20.0 ml of thionyl chloride was heated to reflux. After 150 min, the clear yellow solution was cooled to 30 C. The excess thionyl chloride was distilled off at 50 mm vacuum. After 15 min at 1.0 mm vacuum, the off-white/yellow contents of the flask were taken up in 30 ml of methylene chloride and treated with a slurry of 3.61 g (21.9 mmol) of 3-(4-aminophenyl)propionic acid and 40 ml of isopropanol. The reaction mixture was stirred for 18 hr. The light yellow solid was isolated by filtration and dried in a vacuum oven to give the product.

Compound 70 was also prepared by this method except that acidification was done only to pH 4.56 so as to isolate the free amine.

Method T. Preparation of compound 46. Acetic anhydride (6.45 ml, 6.98 g, 68.4 mmol), 4-hydroxyphenylacetic acid (10.00 g, 65.8 mmol), and xylenes (50 ml) were added to a 100 mL, three-neck flask fitted with a magnetic stir bar, a thermometer, and a Dean-Stark trap with condenser. The flask was heated to reflux, the reaction mixture clearing to a yellow solution around 100 C. Most of the volatile organics (xylenes and acetic acid) were distilled into the Dean-Stark trap over two hours (135-146 C). Distillation was continued for another hour, during which the pot temperature slowly rose to 190° C. and the distillate slowed to a trickle. The residue was poured off while still hot into an aluminum tray. Upon cooling a brown waxy solid formed.

A 2N sodium hydroxide (34.4 ml, 36 g, 68.7 mmol) and 8-aminocaprylic acid (9.94 g, 62.5 mmol) solution was added to a solution of oligo(4-hydroxyphenylacetic acid) (11.06 g, 81.3 mmol) and dioxane (150 ml), added over five minutes. The reaction mixture was heated to 90° C. for 5.5 hours (at which time the reaction was determined to have finished, by HPLC). The clear orange reaction mixture was cooled to 40° C. The dioxane was stripped off in vacuo. The brown residue was taken up in 2N sodium hydroxide, extracted with ethyl acetate (2×100 ml), and acidified. Extraction with ethyl acetate (3×100 ml), decolorizing with carbon, drying over sodium sulfate, and concentration in vacuo gave a brown oil. Trituration with warm water (2 times) and gave a tan solid which was recrystallized twice from ethanol/water to give 2.48 g of the product as a tan solid.

Compounds 106 and 108 were also prepared by this method using the appropriate starting materials.

Method U. Preparation of compound 72. A suspension of 4.11 g (25.3 mmol) of 4-hydroxycoumarin, 4.54 g (25.3 mmol) of 4-(4-aminophenyl)butyric acid, and 20 ml of acetic acid was heated to reflux for 7 days. The reaction mixture was cooled to 25 C, causing an off-white solid to form, which was collected by filtration. The filtrate was diluted with 50 ml of water, causing a second solid to form, which was also collected by filtration. The two solids were combined and recrystallized from 65% ethanol/water to give 0.62 g of product.

Method V. Preparation of compound 85. A slurry of 5.00 g of 10-aminodecanoic acid (26.7 mmol) in 70 mls methylene chloride was treated with 6.78 mls of chlorotrimethylsilane (5.80 g, 53.5 mmol) and was allowed to reflux for 140 min. The reaction mixture was cooled to 0 C and was then treated with 5.58 mls triethylamine (4.1 g, 40.1 mmol). After this mixture stirred for about 20 min, a solution of 3.91 mls of o-fluorobenzoyl chloride (4.24 g, 26.7 mmol) in 10 mls of methylene chloride was added dropwise to the reaction mixture over a period of 15 min. The reaction mixture was allowed to stir for 30 min. at 0 C and then for 18 hrs at 25 C. Methylene chloride was removed in vacuo and 100 mls of NaOH solution (2N) was added to the residue. This mixture was allowed to stir for 1 hr before the mixture was acidified to pH=1 with hydrochloric acid solution (2M). The acidified mixture was then extracted with ethyl acetate (2×100 mls), decolorized with activated carbon, dried over sodium sulfate, and concentrated in vacuo. The resulting white solid was recrystallized from a 50% ethanol/water mixture yielding a white solid, which was allowed to dry for 24 hr in vacuo at 25 C. Yield of product was 6.51 (7.9.5%), mp=85-86 C.

Compounds 86-101 were also prepared by this method by reacting the appropriate amino acid with the appropriate acid chloride.

Method W. Preparation of compound 102. A slurry of 20.72 g of glycine (0.276 mol) in 150 mls methylene chloride was treated with 70.06 mls of chlorotrimethylsilane (59.97 g, 0.552 mol) and was allowed to reflux for 2 hours. The reaction mixture was cooled to 0 C and was then treated with 115.41 mls triethylamine (83.79 g, 0.828 mol). After this mixture stirred for about 20 min, a solution of 20.72 g (0.276 mol) of 4-methoxy-2-acetylbenzoyl chloride (58.70 g, 0.276 mol) in 75 mls of methylene chloride was added dropwise to the reaction mixture over a period of 15 min. The reaction mixture was allowed to stir for 30 min. at 0 C and then for 18 hrs at 25 C. Methylene chloride was removed in vacuo and 200 mls of NaOH solution (2N) was added to the residue. This mixture was allowed to stir for several hours before the mixture was acidified to pH=3 with hydrochloric acid solution (2M). The resulting solids were filtered off and dried in vacuo at 40 C. The solids were recrystallized from water/ethanol (3/1) yielding a solid, which was allowed to dry for 24 hr in vacuo at 25 C. Yield of product was 27.35 g (44%) mp=185.5-189 C.

The sodium salt was made of the above solid by dissolving in 150 mls of ethanol with warming. Sodium hydroxide (4.95 g in 14.5 mL of water) was added to the ethanol solution and cooled to room temperature. The resulting solid was filtered off using heptane to aid filtration and wash solids. After drying a tan solid was obtained (27.73, 92.37%) mp >230 C. CHN calc. for $C_{10}H_{10}N_1O_5Na \cdot 0.40H_2O$: C, 47.21; H, 4.28; N, 5.51; Na, 9.04. found: C, 47.14; H, 4.32; N, 5.36; Na, 8.45 and 2.83% water.

Method X. Preparation of compound 103. A slurry of 25.0 g of β-alanine (0.281 mol) in 300 mls methylene chloride was treated with 71.33 mls of chlorotrimethylsilane (61.06 g, 0.562 mol) and was allowed to reflux for 1.5 hours. The reaction mixture was cooled to 0 C and was then treated with 117.50 mls triethylamine (85.30 g, 0.843 mol). After this mixture stirred for about 20 min, a solution of acetylsalicyloyl chloride (55.73 g, 0.281 mol.) in 150 mls of methylene chloride was added dropwise to the reaction mixture over a period of 15 min. The reaction mixture was allowed to stir for 30 min. at 0 C and then for 18 hrs at 25 C. Methylene chloride was removed in vacuo and 200 mls of NaOH solution (2N) was added to the residue. This mixture was allowed to stir for one hour before the mixture was acidified to pH=1 with sulfuric acid (2M). The resulting oil was extracted with ethyl acetate (3×200 mLs), dried over sodium sulfate and solvent removed in vacuo. The solids were recrystallized from ethyl acetate/hexanes (1/1) yielding a solid, which was allowed to dry for 24 hr in vacuo at 25 C. Yield of product was 9.20 g (16%). CHN calc. for $C_{10}H_{11}N_1O_4$: C, 57.03; H, 5.27; N, 6.67. found: C, 57.41; H, 5.30; N, 6.69. The sodium salt was made of the above solid by dissolving in 50 mls of ethanol with warming. Sodium hydroxide (1.79 g in 5.25 mL of water) was added to the ethanol solution and cooled to room temperature. The resulting solid was filtered off. After drying a solid was obtained (5.80 g) mp 231-235 C. CHN calc. for $C_{10}H_{10}N_1O_4Na.0.35H_2O$: C, 50.56; H, 4.54; N, 5.90; Na, 9.68. found: C, 50.30; H, 4.37; N, 5.72; Na, 9.55 and 2.68% water.

Method Y. Preparation of compound 104. 4-Methoxy salicyclic acid (98.74 g, 0.59 mol) was stirred in methylene chloride (500 ml) while in an ice bath. Triethylamine (123.4 ml, 1.5 eq.) and acetyl chloride (46.2 ml, 1.1 eq) were added dropwise respectively. The solution was removed from the ice bath and stirred at room temperature over two nights. The reaction was followed by HPLC. The reaction mixture was washed with 0.5 N HCl (2×200 ml) and water (2×200 ml). The organic layer was dried over sodium sulfate and reduce in vacuo. The resulting solid was recrystallized in methylene chloride/hexanes. The yield was 61.72 g of the 4-methoxy-2-acetyl benzoic acid. The structure was confirmed by $^1H$ NMR.

To the mixture of 4-methoxy-2-acetyl benzoic acid (20 g, 0.195 mol) and methylene chloride (100 ml), thionyl chloride (13.8 ml, 2 eq) and 1 drop DMF were added. The mixture refluxed for 1.5 hours, then cooled to room temperature and reduced in vacuo yielding an oil. The 4-methoxy-2-acetyl benzoyl chloride was used with no purification.

A slurry of 4-(4-aminophenyl)butyric acid (7.87 g, 0.044 mol) in methylene chloride (100 ml) was treated with TMS chloride (11.2 ml) and was allowed to reflux for 1.5 hours. The reaction mixture was cooled to 0° C. and was then treated with triethylamine (18.4 ml) added dropwise. After this mixture was stirred for about 20 minutes, a solution of the 4-methoxy-2-acetylbenzoyl chloride (10 g) prepared above in methylene chloride (10 ml) was added dropwise to the reaction mixture over a period of 15 minutes. The ice bath was removed and the mixture stirred at room temperature overnight. Methylene chloride was removed in vacuo and 2N NaOH solution (100 ml) was added to the residue. This mixture was allowed to stir for 1 hour before the mixture was acidified to pH=1 with 2M HCl. The acidified mixture was then extracted with ethyl acetate (2×100 ml), decolorized with activated carbon, dried over sodium sulfate, and concentrated in vacuo. The resulting white solid was recrystallized from a 50% ethanol/water mixture yielding a white solid, which was allowed to dry for 24 hours in vacuo at 25 C. CHN calc. for $C_{18}H_{19}NO_5$: C, 65.54; H, 5.81; N, 4.25. found: C, 65.49; H, 5.84; N, 4.23. Yield was 7.76 g (53.6%), mp=177-182 C.

Method Z. Preparation of compound 105. 4-Bromobutyric acid (26.17 g, 0.16 mol) was added to methanol (150 ml) and several drops sulfuric acid were added. This solution was refluxed for 3¼ hours. TLC (1:1 EtOAc/Hex) was done showing the completion of ester formation. The mixture reduced in vacuo to an oil. The oil was dissolved in methylene chloride and washed with water, saturated sodium bicarbonate, and brine. The organic layer was dried over sodium sulfate and reduced in vacuo. The structure was confirmed by $^1H$ NMR and yielded 20.26 g of methyl(4-bromo)butanoate.

6-Chlorocarsalam (12.4 g, 1.12 eq), methyl(4-bromo)butanoate (10.13 g 1.0 eq) and 10.13 g sodium carbonate (10.13 g, 1.12 eq) were stirred in 50 ml DMA. The solution was allowed to reflux for 4.5 hours, and then cooled to room temperature overnight. Solids were filtered off and washed with ethanol. Water and 2N NaOH were added to the filtrate. The mixture was heated for 2.5 hours. An HPLC was performed showing completion of the hydrolysis. The solution was acidified with concentrated HCl to pH of approx. 1. The resulting white solid was filtered off, put over $P_2O_5$ in vacuo overnight. The solid was recrystallized in methanol/water, filtered and dried yielding 7.35 g of compound. CHN calc. For $C_{11}H_{12}NO_4Cl$: C, 51.28; H, 4.69; N, 5.44. found: C, 50.92; H, 4.59; N, 5.46. Melting point 136-140 C. Note that melting points of other batches of this compound made by the same method, showing purer product with elemental analysis, were in the range of 153-155 C.

Method AA. Preparation of compound 118. Sodium carbonate (5.37 g, 0.0506 mol) was added to 250 ml, 3-neck, round bottomed, flask containing 6-chlorocarsalam (10.0 g, 0.0506 mol) and dimethylacetamide (50 ml). Ethyl-5-bromoheptanoate (10.91 g, 0.0460 mol) was added in one portion to the stirring reaction mixture, and heating of the reaction mixture was started. The reaction temperature was maintained at 80° C. and allowed to heat for 16 hr. Heating was discontinued, and the reaction mixture was allowed to cool to room temperature. The reaction mixture was vacuum filtered and the filter cake was washed with two 20 ml portions of ethyl alcohol. Water was added to the filtrate until an orange-brown solid was noted to have precipitated. This solid was isolated by vacuum filtration and was washed first with 20 mls of ethyl alcohol and then with 20 mls of heptane. This solid was transferred to a round bottom flask and 200 ml of 2N NaOH was added. Heating to reflux was started and continued for one hr. The reaction was then cooled to 25 C and the reaction mixture was acidified with 2N HCl solution. The white solid, which precipitated, was isolated by filtration, was recrystallized from 30:70 ethyl alcohol:water and allowed to dry in vacuo overnight. 9.55 g (63.0%) of the product was isolated. Melting point: 115-116 C. Combustion analysis: % C: 56.09 (calc.). 55.93 (found). % H: 6.01. (calc.). 6.09 (found). % N: 4.67. (calc.). 4.64. (found). $^1H$ NMR Analysis: ($d_6$-DMSO): δ 12.7, s, 1H (COOH); δ 12.0, s, 1H (OH); δ 8.88, t, 1H (NH); δ 7.94, d, 1H (H ortho to amide); δ 7.42, dd, 1H (H para to amide); δ 6.92, d, 1H (H ortho to hydroxide); δ 3.27, q, 2H ($CH_2$ alpha to amide); δ 2.20, t, 2H ($CH_2$ alpha to COOH); δ 1.40, m, 4H ($CH_2$ beta to amide, $CH_2$ beta to COOH); δ 1.30, m, 4H (remaining aliphatic $CH_2$).

Compounds 114, 116 and 117 were also prepared by this method using the appropriate starting materials.

Method BB: Preparation of compound 121. A suspension of 2 amino-4-chlorophenol (17.88 g, 124.5 mmol), 8-ethoxy-8-oxooctanoic acid (25.19 g, 124.5 mmol), boric acid (0.385 g, 6.23 mmol), and 2-amino-5-methylpyridine (0.675 g, 6.23 mmol) in 160 mL of dried toluene was heated at reflux (110 C) under nitrogen for 4 hour during which water (2.5 mL) produced in the reaction was removed by azeotropic distillation in a Dean-Stark separation unit. Thin layer chromatography on silica gel (eluant: EtOAc/heptane: 1/1) revealed the complete reaction. To the cooled reaction mixture was added a 2N aqueous solution of NaOH (125 mL, 250 mmol). The reaction was heated at reflux for 4 h, then cooled. The cooled reaction mixture was diluted with ethyl acetate (300 mL) and water (150 mL). The aqueous layer was washed with two portions of ethyl acetate (250 mL). After careful separation, the aqueous layer was chilled and acidified with a 10% solution of hydrochloric acid (86.20 mL, 250 mmol) to afford a solid which was filtered, washed with hexane, and dried under vacuum. Trituration with dichloromethane afforded the desired acid (8-(5-Chloro-2-hydroxyanilino)-8-oxooctanoic acid) (22.39 g, 60%). as an off-white solid: HPLC (Column: Higgins Kromasil 100 C18, water/acetonitrile/acetic acid: 950/50/1, 3 mL/min, 220 nm) $R_t$ 5.38 min.; mp 123-124 C; $^1H$ NMR (DMSO $d_6$, 300 MHz) δ: 1.28 (m, 4H), 1.51 (m, 4H), 2.19 (t, 2H), 2.39 (t, 2H), 6.83 (d, 1H), 6.93 (dd, 1H), 7.95 (d, 1H), 9.20 (s, 1H), 10.10 (s, 1H), 12.00 (br s, 1H); $^{13}C$ NMR (DMSO $d_6$, 75 MHz) δ: 24.29, 24.90, 28,20, 33.58, 35.90, 116.50, 121.02, 122.20, 123.41, 127.74, 148.23, 171.93, 174.26. MS m/z 300 (M+1)$^+$. Anal. Calcd for $C_{14}H_{18}ClNO_4$: C, 56.10; H, 6.05; Cl, 11.83, N, 4.67. Found: C, 56.07; H, 6.11, 11.98; N, 4.64.

Compound 119 was prepared by the same method using the appropriate starting materials. Compounds 124-130 can also be prepared using this method with the appropriate starting materials.

Example 2

Parathyroid Hormone Delivery

Oral gavage (PO) or intracolonic (IC) dosing solutions of delivery agent compound and parathyroid hormone residues 1-34 (PTH) (residues 1-38 for the solution with compound 103) were prepared. A solution of the compound was made either with the sodium salt of the compound or by converting the free acid to its sodium salt by making a solution of the compound, stirring, adding one equivalent of sodium hydroxide (1.0 N), and diluting with water (for PO solutions) or 25% aqueous propylene glycol (for IC). The final dosing solutions were prepared by mixing the compound solution with a PTH stock solution (typically having a concentration of 5 mg PTH/ml) and diluting to the desired volume (usually 3.0 ml). The compound and PTH dose amounts are listed in Table 1 below.

Male Sprague-Dawley rats weighing between 200-250 g were fasted for 24 hours and were administered ketamine (44 mg/kg) and chlorpromazine (1.5 mg/kg) 15 minutes prior to dosing. The rats were administered one of the dosing solutions at 1 ml/kg for PO or 0.5 ml/kg for IC. Blood samples were collected serially from the tail artery for serum determination of PTH concentration. Serum PTH concentrations were quantified by a PTH radioimmunoassay kit (Kit # RIK 6101 from Peninsula Laboratories, Inc., San Carlos, Calif.). Results are illustrated in Table 1, below.

TABLE 1

PTH Delivery in Rats - oral (PO) and intracolonic (IC)

| Compound | Method of Administration | Compound Dose (mg/kg) | PTH Dose (μg/kg) | Mean Peak Serum PTH (pg/mL) |
|---|---|---|---|---|
| 3 | PO | 300 | 100 | 222 ± 155 |
| 10 | PO | 300 | 100 | 420 ± 335 |
| 79 | IC | 100 | 25 | 731 ± 577 |
| 80 | IC | 100 | 25 | 1456 ± 486 |
| 86 | PO | 100 | 200 | 0 |
| 89 | PO | 100 | 200 | 27 ± 61 |
| 90 | PO | 100 | 200 | 14 ± 21 |
| 91 | PO | 100 | 200 | 5 ± 12 |
| 92 | PO | 100 | 200 | 303 ± 427 |
| 93 | PO | 100 | 200 | 343 ± 155 |
| 94 | PO | 100 | 200 | 17 ± 38 |
| 102 | PO | 100 | 200 | 252.13 ± 230.46 |
| 102 | PO | 100 | 200 | 70.98 ± 81.81 |
| 102 | PO | 100 | 200 | 894.82 ± 702.01 |
| 102 | PO | 100 | 200 | 185.52 ± 59.47 |
| 103 | IC | 100 | 25 | 38.53 ± 30.9 |
| 104 | PO | 100 | 200 | 286.35 ± 191.58 |
| 106 | PO | 100 | 200 | 309.07 ± 289.74 |
| 106 | PO | 100 | 200 | 894.91 ± 1220.06 |
| 106 | PO | 100 | 200 | 1459.71 ± 1041.36 |
| 106 | PO | 100 | 200 | 192.15 ± 48.81 |
| 107 | PO | 100 | 200 | 110.19 ± 142.23 |
| 107 | PO | 100 | 200 | 254.71 ± 191.97 |
| 107 | PO | 100 | 200 | 1302.99 ± 871.82 |
| 107 | PO | 100 | 200 | 304.8 ± 381.39 |

Example 3

Heparin Delivery

Intracolonic dosing (IC) compositions containing delivery agent compound and heparin sodium USP in 25% aqueous propylene glycol were prepared by mixing. Either the sodium salt of the compound was used or the free acid was converted to the sodium salt with one equivalent of sodium hydroxide (1.0 N). Typically, compound and heparin powders were mixed, 25% aqueous propylene glycol was added, NaOH solution was added, the contents sonicated, then diluted to a volume of 3.0. pH was checked and adjusted if necessary to pH=7-8. The final compound and heparin dose amounts are listed in Table 2 below.

Male Sprague-Dawley rats weighing between 200-250 g were fasted for 24 hours and were administered ketamine (44 mg/kg) and chlorpromazine (1.5 mg/kg) 15 minutes prior to dosing. The dosing solutions were administered to fasted rats at a volume dose of 1 ml/kg. Blood samples were collected by cardiac puncture following the administration of ketamine (44 mg/kg). Heparin activity was determined utilizing the activated partial thromboplastin time (APTT) according to the method of Henry, J. B., Clinical Diagnosis and Management by Laboratory Methods; Philadelphia, Pa.; W. B. Saunders (1979). Results are given in Table 2, below.

TABLE 2

Intracolonic Delivery of Heparin

| Compound | Method of Administration | Compound Dose (mg/kg) | Heparin Dose (mg/kg) | Mean Peak APTT (sec) |
|---|---|---|---|---|
| 7 | IC | 50 | 25 | 59 ± 41 |
| 14 | IC | 50 | 25 | 54 ± 21 |
| 28 | IC | 50 | 25 | 55 ± 27 |
| 33 | IC | 50 | 25 | 42 ± 21 |
| 34 | IC | 50 | 25 | 58 ± 31 |
| 35 | IC | 50 | 25 | 154 ± 171 |
| 41 | IC | 50 | 25 | 41 ± 26 |
| 46 | IC | 50 | 25 | 52 ± 34 |
| 48 | IC | 50 | 25 | 75 ± 18 |
| 51 | IC | 50 | 25 | 111 ± 49 |
| 54 | IC | 50 | 25 | 124 ± 137 |
| 55 | IC | 50 | 25 | 125 ± 195 |
| 56 | IC | 50 | 25 | 91 ± 75 |
| 60 | IC | 50 | 25 | 71 ± 43 |
| 72 | IC | 50 | 25 | 50 ± 18 |
| 85 | IC | 50 | 25 | 27 ± 4 |
| 86 | IC | 50 | 25 | 24 ± 1 |
| 86 | IC | 50 | 25 | 31 ± 11 |
| 87 | IC | 50 | 25 | 21 ± 1 |
| 87 | IC | 50 | 25 | 23 ± 3 |
| 88 | IC | 50 | 25 | 59 ± 47 |
| 89 | IC | 50 | 25 | 33 ± 7 |
| 90 | IC | 50 | 25 | 26 ± 7 |
| 91 | IC | 50 | 25 | 24 ± 4 |
| 92 | IC | 50 | 25 | 22 ± 2 |
| 93 | IC | 25 | 50 | 22 ± 0 |
| 94 | IC | 50 | 25 | 50 ± 28 |
| 95 | IC | 50 | 25 | 30 ± 2 |
| 96 | IC | 50 | 25 | 72 ± 63 |
| 97 | IC | 50 | 25 | 33 ± 10 |
| 98 | IC | 50 | 25 | 25 ± 5 |
| 99 | IC | 50 | 25 | 34 ± 7 |
| 100 | IC | 50 | 25 | 31 ± 8 |
| 101 | IC | 50 | 25 | 26 ± 5 |
| 102 | IC | 50 | 25 | 24.8 ± 0.9 |
| 102 | IC | 50 | 25 | 24.7 ± 6.5 |
| 103 | IC | 50 | 25 | 21.9 ± 2.0 |
| 106 | IC | 50 | 25 | 48 ± 16.9 |
| 106 | IC | 50 | 25 | 27.7 ± 12.6 |
| 107 | IC | 50 | 25 | 26.2 ± 6.1 |

TABLE 2-continued

Intracolonic Delivery of Heparin

| Compound | Method of Administration | Compound Dose (mg/kg) | Heparin Dose (mg/kg) | Mean Peak APTT (sec) |
|---|---|---|---|---|
| 108 | IC | 50 | 25 | 72.9 ± 28.9 |
| 109 | IC | 50 | 25 | 24.2 ± 1.7 |
| 110 | IC | 50 | 25 | 26.5 ± 4.7 |
| 110 | IC | 50 | 25 | 23.4 ± 0.7 |
| 111 | IC | 50 | 25 | 24.4 ± 3.3 |
| 112 | IC | 50 | 25 | 28.7 ± 11.5 |
| 113 | IC | 50 | 25 | 20.4 |
| 120 | IC | 50 | 25 | 42 ± 34 |
| 131 | IC | 50 | 25 | 58 ± 30 |
| 132 | IC | 50 | 25 | 65 ± 19 |

Example 4

Recombinant Human Growth Hormone (rhGH) Oral Delivery

Oral gavage (PO) dosing solutions of delivery agent compound and rhGH in phosphate buffer were prepared. A solution of the compound was made either with the sodium salt of the compound or by converting the free acid to its sodium salt by making a solution of the compound, stirring, adding one equivalent of sodium hydroxide (1.0 N), and diluting with phosphate buffer. The final dosing solutions were prepared by mixing the compound solution with an rhGH stock solution (typically having a concentration of 15 mg rhGH/ml) and diluting to the desired volume (usually 3.0 ml). The compound and rhGH dose amounts are listed in Table 3 below.

Male Sprague-Dawley rats weighing 200-250 g were fasted for 24 hours and administered ketamine (44 mg/kg) and chlorpromazine (1.5 mg/kg) 15 minutes prior to dosing. The rats were administered 1 ml/kg of the dosing solution. Blood samples were collected serially from the tail artery for determination of serum rhGH concentrations. Serum rhGH concentrations were quantified by an rhGH immunoassay test kit (Kit # KIF4015 from Genzyme Corporation Inc., Cambridge, Mass.).

TABLE 3

Oral Delivery of rhGH in Rats

| Compound | Method of Administration | Compound Dose (mg/kg) | rhGH Dose (mg/kg) | Mean Peak Serum [rhGH] (ng/ml) |
|---|---|---|---|---|
| 3 | PO | 300 | 6 | 72 ± 45 |
| 10 | PO | 200 | 3 | 43 ± 65 |
| 40 | PO | 300 | 6 | 42 ± 80 |
| 45 | PO | 200 | 3 | 49 ± 56 |
| 54 | PO | 200 | 3 | 48 ± 33 |
| 74 | PO | 200 | 3 | 80 ± 44 |
| 76 | PO | 200 | 3 | 40 ± 34 |
| 77 | PO | 200 | 3 | 54 ± 62 |

Example 5

Salmon Calcitonin (sCT) Delivery

Oral dosing (PO) compositions of delivery agent compound and salmon calcitonin (sCT) in water were prepared by mixing. The amounts are listed in Table 4. 450 mg of compound was added to 2.0 ml of water. Either the sodium salt of the compound was used or the free acid was converted to the sodium salt by stirring the resultant solution and adding one equivalent of sodium hydroxide (1.0 N) and diluting with water. 90 µg sCT was added to the solution. Water was then added to bring the total volume to 3.0 ml. The solution had a final compound concentration of 150 mg/ml. (For compounds 118 and 123, the solutions were diluted to 6.0 ml and the volume dose was doubled.) The total sCT concentration was 30 µg/ml. (For compound 123, a different amount of sCT was used to result in the final sCT dose of 100 µg/kg when 2.0 ml/kg was dosed.)

Male Sprague-Dawley rats weighing between 200-25.0 g were fasted for 24 hours and were administered ketamine (44 mg/kg) and chlorpromazine (1.5 mg/kg) 15 minutes prior to dosing. The rats were administered 1 ml/kg of dosing solution (2 ml/kg for compounds 118 and 123). Blood samples were collected serially from the tail artery. Serum sCT was determined by testing with an EIA kit (Kit # EIAS-6003 from Peninsula Laboratories, Inc., San Carlos, Calif.). The standard protocol from the kit was modified for compounds 104 and 105 as follows: incubated with 50 µl peptide antibody for 2 hours with shaking in the dark, washed the plate, added serum and biotinylated peptide and diluted with 4 ml buffer, and shook overnight in the dark. Results are illustrated in Table 4, below.

TABLE 4

Oral Delivery of Salmon Calcitonin (sCT) in Rats

| Compound | Compound dose (mg/kg) | sCT Dose (µg/kg) | Serum sCT (pg/ml) ± SD (SE) |
|---|---|---|---|
| 104 | 50 | 25 | 287 ± 104 |
| 105 | 50 | 25 | 583 ± 140 |
| 105 | 150 | 30 | 802 ± 669 (299) |
| 116 | 150 | 30 | 724 ± 463 (207) |
| 117 | 150 | 30 | 383 ± 292 (131) |
| 118 | 150 | 30 | 276 ± 319 (159) |
| 119 | 150 | 30 | 95 ± 119 (53) |
| 121 | 150 | 30 | 717 ± 603 (301) |
| 122 | 150 | 30 | 187 ± 79 (36) |
| 123 | 150 | 100 | 0 |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound represented by the formula:

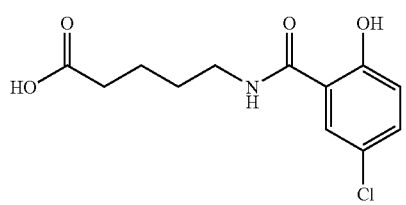

or a pharmaceutically acceptable salt thereof.

2. The compound of claim 1 wherein the pharmaceutically acceptable salt is sodium salt.

3. A composition comprising:
(A) at least one biologically active agent; and
(B) the compound of claim 1.

4. The compound of claim 3 wherein the pharmaceutically acceptable salt is sodium salt.

5. The composition of defined in claim 3, wherein said biologically active agent comprises at least one protein, polypeptide, peptide, hormone, polysaccharide, mucopolysaccharide, carbohydrate, or lipid.

6. The composition of claim 5, wherein said biologically active agent comprises a protein, polypeptide or peptide.

7. The composition of claim 5, wherein said biologically active agent comprises a mucopolysaccharide.

8. The composition of claim 3, wherein said biologically active agent is selected from the group consisting of: growth hormone, growth hormone-releasing hormones, interferons, interleukin-1, interleukin-2, insulin, insulin-like growth factor (IGF), heparin, calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, vancomycin, desferrioxamine (DFO), parathyroid hormone (PTH), antimicrobials, anti-fungal agents; analogs, fragments, mimetics and polyethylene glycol (PEG)-modified derivatives of these compounds; and any combination thereof.

9. The composition of claim 8, wherein said biologically active agent is selected from a growth hormone, interferon, insulin, heparin, cromolyn sodium, an antigen, an anti-microbial agent, calcitonin, parathyroid hormone, erythropoietin, and combinations thereof.

10. The composition of claim 9, wherein said growth hormone is selected from human growth hormones (hGH), recombinant human growth hormones (rhGH), bovine growth hormones, porcine growth hormones, or a combination thereof.

11. The composition of claim 8, wherein said biologically active agent is interferon.

12. The composition of claim 8, wherein said biologically active agent is insulin.

13. The composition of claim 8, wherein said insulin is selected from porcine insulin, bovine insulin, human insulin, and human recombinant insulin.

14. The composition of claim 8, wherein said biologically active agent is heparin.

15. The composition of claim 14, wherein said heparin is selected from low molecular weight heparin, very low molecular weight heparin, ultra low molecular weight heparin, heparinoids, dermatans, chondroitins, or a combination thereof.

16. The composition of claim 15, wherein said biologically active agent is low molecular weight heparin.

17. The composition of claim 8, wherein said biologically active agent is cromolyn sodium.

18. The composition of claim 17, wherein said cromolyn sodium is selected from sodium chromoglycate, disodium chromoglycate or a combination thereof.

19. The composition of claim 8, wherein said biologically active agent is an antigen.

20. The composition of claim 8, wherein said biologically active agent is an anti-microbial agent.

21. The composition of claim 8, wherein said biologically active agent is a calcitonin.

22. The composition of claim 21, wherein said calcitonin is selected from salmon calcitonin, eel calcitonin, human calcitonin or a combination thereof.

23. The composition of claim 8, wherein said biologically active agent is parathyroid hormone.

24. The composition of claim 8, wherein said biologically active agent is erythropoietin.

25. A dosage unit form comprising
(A) a composition as defined in claim 3; and
(B) (a) an excipient
  (b) a diluent,
  (c) a disintegrant,
  (d) a lubricant,
  (e) a plasticizer,
  (f) a colorant,
  (g) a dosing vehicle, or
  (h) any combination thereof.

26. The dosage unit form of claim 25 wherein the pharmaceutically acceptable salt is the sodium salt.

27. The dosage unit form of claim 25, comprising a powder.

28. The dosage unit form of claim 25 comprising a tablet.

29. The dosage unit form of claim 25 comprising a capsule.

30. The dosage unit form of claim 25 comprising a liquid.

31. The dosage unit form of claim 25, wherein said biologically active agent comprises at least one protein, polypeptide, peptide, hormone, polysaccharide, mucopolysaccharide, carbohydrate, or lipid.

32. The dosage unit form of claim 31, wherein said biologically active agent comprises a protein, polypeptide, or peptide.

33. The dosage unit form of claim 31, wherein said biologically active agent comprises a mucopolysaccharide.

34. The dosage unit form of claim 25, wherein said dosing vehicle is selected from the group consisting of water, 1,2-propane diol, ethanol, olive oil or any combination thereof.

35. The dosage unit form of claim 25, wherein said biologically active agent is selected from the group consisting of: growth hormone, growth hormone-releasing hormones, interferons, interleukin-1, interleukin-2, insulin, insulin-like growth factor (IGF), heparin, calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, vancomycin, desferrioxamine (DFO), parathyroid hormone (PTH), antimicrobials, anti-fungal agents; analogs, fragments, mimetics and polyethylene glycol (PEG)-modified derivatives of these compounds; and any combination thereof.

36. The dosage unit form of claim 35, wherein said biologically active agent is selected from a growth hormone, interferon, insulin, heparin, cromolyn sodium, an antigen, an anti-microbial agent, calcitonin, parathyroid hormone, erythropoietin, and combinations thereof.

37. The dosage unit form of claim 35, wherein said growth hormone is selected from human growth hormones (hGH), recombinant human growth hormones (rhGH), bovine growth hormones, porcine growth hormones, or a combination thereof.

38. The dosage unit form of claim 35, wherein said biologically active agent is interferon.

39. The dosage unit form of claim 35, wherein said biologically active agent is insulin.

40. The dosage unit form of claim 39, wherein said insulin is selected from porcine insulin, bovine insulin, human insulin, and human recombinant insulin.

41. The dosage unit form of claim 35, wherein said biologically active agent is heparin.

42. The composition of claim 41, wherein said heparin is selected from low molecular weight heparin, very low molecular weight heparin, ultra low molecular weight heparin, heparinoids, dermatans, chondroitins, or a combination thereof.

43. The dosage unit form of claim 42, wherein said biologically active agent is low molecular weight heparin.

44. The dosage unit form of claim 35, wherein said biologically active agent is cromolyn sodium.

45. The dosage unit form of claim 44, wherein said cromolyn sodium is selected from sodium chromoglycate, disodium chromoglycate or a combination thereof.

46. The dosage unit form of claim 35, wherein said biologically active agent is an antigen.

47. The dosage unit form of claim 35, wherein said biologically active agent is an anti-microbial agent.

48. The dosage unit form of claim 35, wherein said biologically active agent is calcitonin.

49. The dosage unit form of claim 35, wherein said calcitonin is selected from salmon calcitonin, eel calcitonin, human calcitonin or a combination thereof.

50. The dosage unit form of claim 35, wherein said biologically active agent is parathyroid hormone.

51. The dosage unit form of claim 35, wherein said biologically active agent is erythropoietin.

52. A method for administering a biologically active agent to an animal, said method comprising administering to said animal the composition of claim 3.

53. The method of claim 52 wherein the pharmaceutically acceptable salt is the sodium salt.

54. The method of claim 52, wherein said biologically active agent is administered by a route selected from: oral, intranasal, sublingual, intraduodenal, subcutaneous, buccal, intracolonic, rectal, vaginal, mucosal, pulmonary, transdermal, intradermal, parenteral, intravenous, intramuscular and intraocular.

55. The method of claim 52, wherein said biologically active agent is administered by the oral route.

56. The method of claim 52, wherein said biologically active agent comprises at least one protein, polypeptide, peptide, hormone, polysaccharide, mucopolysaccharide, carbohydrate, or lipid.

57. The method of claim 56, wherein said biologically active agent comprises a protein, polypeptide, or peptide.

58. The method of claim 56, wherein said biologically active agent comprises a mucopolysaccharide.

59. The method of claim 52, wherein said biologically active agent is selected from the group consisting of: growth hormone, growth hormone-releasing hormones, interferons, interleukin-1, interleukin-2, insulin, insulin-like growth factor (IGF), heparin, calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, vancomycin, desferrioxamine (DFO), parathyroid hormone (PTH), anti-microbials, anti-fungal agents; analogs, fragments, mimetics and polyethylene glycol (PEG)-modified derivatives of these compounds; and any combination thereof.

60. The method of claim 59, wherein said biologically active agent is selected from a growth hormone, interferon, insulin, heparin, cromolyn sodium, an antigen, an anti-microbial agent, calcitonin, parathyroid hormone, erythropoietin, and combinations thereof.

61. The method of claim 59, wherein said growth hormone is selected from human growth hormones (hGH), recombinant human growth hormones (rhGH), bovine growth hormones, porcine growth hormones, or a combination thereof.

62. The method of claim 59, wherein said biologically active agent is interferon.

63. The method of claim 59, wherein said biologically active agent is insulin.

64. The method of claim 63, wherein said insulin is selected from porcine insulin, bovine insulin, human insulin, and human recombinant insulin.

65. The method of claim 59, wherein said biologically active agent comprises heparin.

66. The method of claim 65, wherein said heparin is selected from low molecular weight heparin, very low molecular weight heparin, ultra low molecular weight heparin, heparinoids, dermatans, chondroitins, or a combination thereof.

67. The method of claim 66, wherein said biologically active agent is low molecular weight heparin.

68. The method of claim 59, wherein said biologically active agent is cromolyn sodium.

69. The method of claim 68, wherein said cromolyn sodium is sodium chromoglycate, disodium chromoglycate or a combination thereof.

70. The method of claim 59, wherein said biologically active agent is an antigen.

71. The method of claim 43, wherein said biologically active agent is an anti-microbial agent.

72. The method of claim 43, wherein said biologically active agent is calcitonin.

73. The method of claim 43, wherein said calcitonin is selected from salmon calcitonin, eel calcitonin, human calcitonin or a combination thereof.

74. The method of claim 43, wherein said biologically active agent is parathyroid hormone.

75. The method of claim 43, wherein said biologically active agent is erythropoietin.

76. A method for preparing a composition, said method comprising mixing:
(A) at least one biologically active agent;
(B) at least one compound as defined in claim 1; and
(C) optionally, a dosing vehicle.

77. The method of claim 76 wherein the pharmaceutically acceptable salt is sodium salt.

78. The method of claim 76, wherein said biologically active agent comprises at least one protein, polypeptide, peptide, hormone, polysaccharide, mucopolysaccharide, carbohydrate, or lipid.

79. The method of claim 78, wherein said biologically active agent comprises a protein, polypeptide, or peptide.

80. The method of claim 78, wherein said biologically active agent comprises a mucopolysaccharide.

81. The method of claim 76, wherein said biologically active agent is selected from the group consisting of: growth hormone, growth hormone-releasing hormones, interferons, interleukin-1, interleukin-2, insulin, insulin-like growth factor (IGF), heparin, calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, vancomycin, desferrioxamine (DFO), parathyroid hormone (PTH), anti-microbials, anti-fungal agents; analogs, fragments, mimetics and polyethylene glycol (PEG)-modified derivatives of these compounds; and any combination thereof.

* * * * *